United States Patent
Wissenwasser et al.

(10) Patent No.: US 9,833,620 B2
(45) Date of Patent: Dec. 5, 2017

(54) ACTIVE TELEMETRY RESPONSE FOR HEARING IMPLANTS

(71) Applicant: MED-EL Elektromedizinische Geraete GmbH, Innsbruck (AT)

(72) Inventors: Jürgen Wissenwasser, Innsbruck (AT); Andreas Mitterer, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 15/103,365

(22) PCT Filed: Dec. 18, 2014

(86) PCT No.: PCT/US2014/071063
§ 371 (c)(1),
(2) Date: Jun. 10, 2016

(87) PCT Pub. No.: WO2015/095469
PCT Pub. Date: Jun. 25, 2015

(65) Prior Publication Data
US 2016/0310735 A1    Oct. 27, 2016

Related U.S. Application Data

(60) Provisional application No. 61/918,911, filed on Dec. 20, 2013.

(51) Int. Cl.
*A61N 1/00* (2006.01)
*A61N 1/36* (2006.01)
(Continued)

(52) U.S. Cl.
CPC ..... *A61N 1/36032* (2013.01); *A61N 1/37223* (2013.01); *H04R 25/554* (2013.01); *H04R 2225/67* (2013.01)

(58) Field of Classification Search
CPC ....... A61N 1/36032; A61N 1/37211–1/37241; A61N 1/37282; A61N 1/37288; H04R 25/554
See application file for complete search history.

(56) References Cited

U.S. PATENT DOCUMENTS 5,758,651 A   6/1998  Nygard et al.
6,157,861 A   12/2000 Faltys et al.
(Continued)

OTHER PUBLICATIONS

International Searching Authority, International Search Report for International Application No. PCT/US2014/071063, dated Mar. 9, 2015, together with the Written Opinion of the International Searching Authority, 17 pages.

*Primary Examiner* — Scott Getzow
(74) *Attorney, Agent, or Firm* — Sunstein Kann Murphy & Timbers LLP

(57) ABSTRACT

An implantable processor arrangement is described for an active implantable medical device (AIMD) system implanted under the skin of a patient. An implantable communications coil arrangement is configured for transdermal transfer of an implant communications signal. An implantable processor is coupled to and controls the implantable communications coil arrangement so as to operate in two different communications modes. In a normal operation mode, the processor configures the communications coil arrangement for peridermal communication with an external communications coil placed on the skin of the patient immediately over the implantable communications coil arrangement. In a long range telemetry mode, the processor configures the communications coil arrangement for extradermal communication with an external telemetry coil located distant from the skin of the patient immediately over the implantable communications coil arrangement.

18 Claims, 3 Drawing Sheets

(51) Int. Cl.
*A61N 1/372* (2006.01)
*H04R 25/00* (2006.01)

(56) References Cited

U.S. PATENT DOCUMENTS

| | | |
|---|---|---|
| 7,248,926 B2 | 7/2007 | Woods et al. |
| 2007/0036280 A1* | 2/2007 | Roeck .................. H04R 25/554 379/52 |
| 2011/0009924 A1* | 1/2011 | Meskens ............ A61N 1/36032 607/57 |
| 2011/0160808 A1 | 6/2011 | Lyden et al. |
| 2012/0109256 A1 | 5/2012 | Meskins et al. |

* cited by examiner

ACTIVE TELEMETRY RESPONSE FOR HEARING IMPLANTS

This application is a national phase entry of Patent Cooperation Treaty Application PCT/US2014/071063, filed Dec. 18, 2014, which in turn claims priority from U.S. Provisional Patent Application 61/918,911, filed Dec. 20, 2013, which is incorporated herein by reference.

FIELD OF THE INVENTION

The present invention relates to active implantable medical device (AIMD) systems for example neuro stimulation devices and without limitation such as cochlear implants, laryngeal or heart pacemakers, and more specifically to telemetry communication in such systems.

BACKGROUND ART

In some AIMD systems such as commercially available cochlear implant systems, Spinal Cord Stimulator (SCS) systems, all of the data communications and power supply requirements are met via a close transcutaneous arrangement with an external transmission coil placed on the skin directly over the implanted receiver coil such as described, for example, in U.S. Patent Publication 2012/0109256, which is incorporated herein by reference in its entirety. In other types of AIMD systems such as Implantable Cardiac Defibrillators (ICD) and Heart Pacemakers (PM) have primary galvanic cells as power source and for telemetry purposes use either a coil arrangement as described above, or else an RF link in the Medical Implant Communication Service (MICS) frequency band (402 to 405 MHz) that requires a separate IC and a matched antenna (coil). For the sole purpose of data transfer, MICS transceivers are more compact than an inductive coil system and these devices work at a distance of up to 2 m and so can be utilized in the surgical operating theatre. A major task is to keep the power consumption of the device small so that the overall lifetime of an implant with a primary cell is not significantly reduced.

In AIMD systems that use an inductive communication coil arrangement, telemetry data from the implanted components back across the skin to the outside is typically performed using load modulation of the receiver coil arrangement to modulate the load on the external transmitter coil. That requires the external coil to be in close vicinity to the implanted coil, which during implantation surgery can only be achieved if the external coil is placed in a sterile package and is then positioned close to the open surgical wound. That limits the freedom of the physician/surgeon to manipulate the implant, e.g. optimizing the implant or electrode position while the implant is operating.

One typical example of an AIMD system is a cochlear implant. A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid filled cochlea 104 functions as a transducer to generate electric pulses that are transmitted to the cochlear nerve 113, and ultimately to the brain. Hearing is impaired when there are problems in the ability to transduce external sounds into meaningful action potentials along the neural substrate of the cochlea 104.

In some cases of hearing impairment, a cochlear implant AIMD system may be provided that electrically stimulates auditory nerve tissue with small currents delivered by multiple electrode contacts distributed along an implant electrode. FIG. 1 shows some components of a typical cochlear implant system where an external microphone provides an audio signal input to an external signal processor 111 which implements one of various known signal processing schemes. The processed signal is converted by the external signal processor 111 into a digital data format, such as a sequence of data frames, for transmission by an external transmitter coil 107 across the skin into a receiver processor in a stimulator processor 108. The stimulator processor 108 extracts the audio information in the received signal and also a power component that provides electrical power for the implanted parts of the system. The receiver processor in the stimulator processor 108 may perform additional signal processing such as error correction, pulse formation, etc., and produces a stimulation pattern (based on the extracted audio information) that is sent through connected wires 109 to an implant electrode 110. Typically, the implant electrode 110 includes multiple electrodes 112 on its surface that provide selective stimulation of the cochlea 104.

SUMMARY OF THE INVENTION

Embodiments of the present invention are directed to an implantable processor arrangement for an AIMD system implanted under the skin of a patient; e.g., a cochlear implant system. An implantable communications coil arrangement is configured for transdermal transfer of an implant communications signal. An implantable processor is coupled to and controls the implantable communications coil arrangement so as to operate in two different communications modes. In a normal operation mode the processor configures the communications coil arrangement for peridermal communication with an external communications coil placed on or close to the skin of the patient immediately over the implantable communications coil arrangement. In a long range telemetry mode the processor configures the communications coil arrangement for extradermal communication with an external telemetry coil located distant from the skin of the patient immediately over the implantable communications coil arrangement.

Embodiments of the present invention also include a fitting system for an AIMD system; e.g., a cochlear implant system. An external fitting module is configured to perform a patient fitting process that adjusts an implanted AIMD processor to reflect patient-specific performance characteristics. The AIMD processor controls two different communications modes. In a normal operation mode the processor configures an implanted communications coil arrangement for peridermal communication of an implant communications signal with an external communications coil placed on the skin of the implanted patient immediately over the implanted communications coil arrangement for normal operation of the AIMD system. In a long range telemetry mode the processor configures the implanted communications coil arrangement for extradermal communication with an external telemetry coil located distant from the skin of the implanted patient immediately over the implantable communications coil arrangement. And the patient fitting process includes interaction of the external fitting module via the external telemetry coil with the AIMD processor in the long range telemetry mode to adjust the operation of the AIMD processor in the normal operation mode based on the patient-specific performance characteristics.

Embodiments of the present invention also include a testing system for use during surgical implantation of an AIMD system; e.g., a cochlear implant system. An implantable communications coil arrangement is configured for transdermal transfer of an implant communications signal. An implantable processor is coupled to and controls the implantable communications coil arrangement so as to operate in two different communications modes. In a normal operation mode, the processor configures the communications coil arrangement for peridermal communication with an external communications coil placed on the skin of the implanted patient immediately over the implantable communications coil arrangement. In a long range telemetry mode, the processor configures the communications coil arrangement for extradermal communication with an external telemetry coil located distant from the skin of the implanted patient immediately over the implantable communications coil arrangement.

In specific embodiments of any of the foregoing, the extradermal communication in the long range telemetry mode may include communication of an implant programming signal received by the implantable communications coil arrangement, and/or an implant telemetry signal transmitted by the implantable communications coil arrangement. The implantable processor may control operation in the long range telemetry mode to be limited in initiation to periodic intervals, and/or by software control during a defined wake-up procedure.

DETAILED DESCRIPTION OF SPECIFIC EMBODIMENTS

In AIMD systems which include a signal receiver coil, e.g. for recharging an implant battery, that battery can be used by the implanted processor as a power source to produce an alternating magnetic field utilizing the implant coil. The produced field can be modulated and detected by an external coil that can be distant from the skin immediately over the implant. Thus embodiments of the present invention are directed an AIMD system that operates an implanted active driven circuit L-C transmitter using existing load-modulation components. So the parallel or serial L-C resonance circuit that is normally available for load modulation or energy transfer to the implant is used for signal transmission beyond the peridermal region near the skin covering the implant. This makes efficient use of already available existing elements from the load modulator to solve the problem of a long-distance back telemetry RF-link that is not achievable by conventional load-modulation. Besides the implanted system components as such, embodiments also include a testing system for use during surgical implantation of an AIMD system which includes an implantable processor having such an active telemetry response mode, as well as a post-surgical fitting system for patient-specific fitting of an AIMD system having such an active telemetry response mode.

Figure 1:
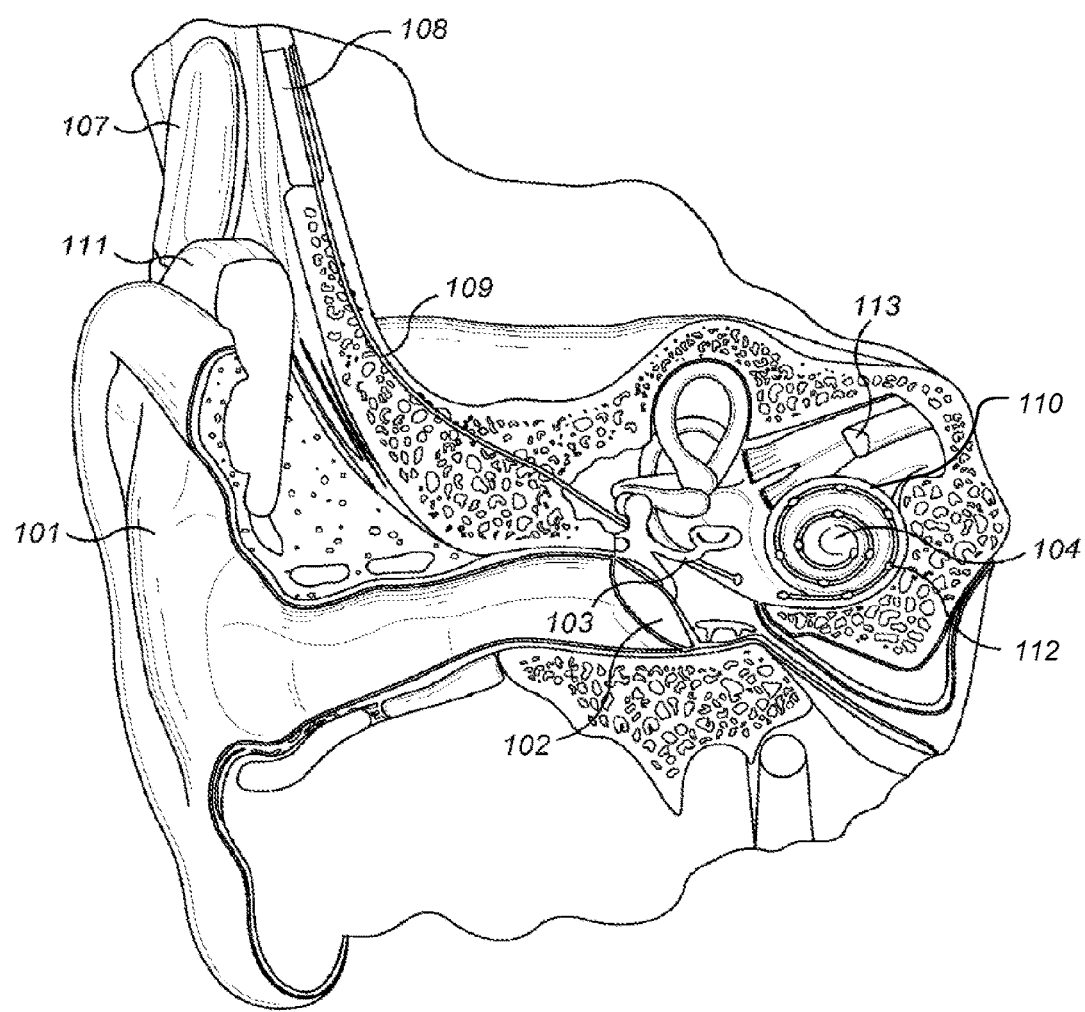
FIG. 1 shows anatomical features of a typical human ear having a cochlear implant system.
Figure 2:
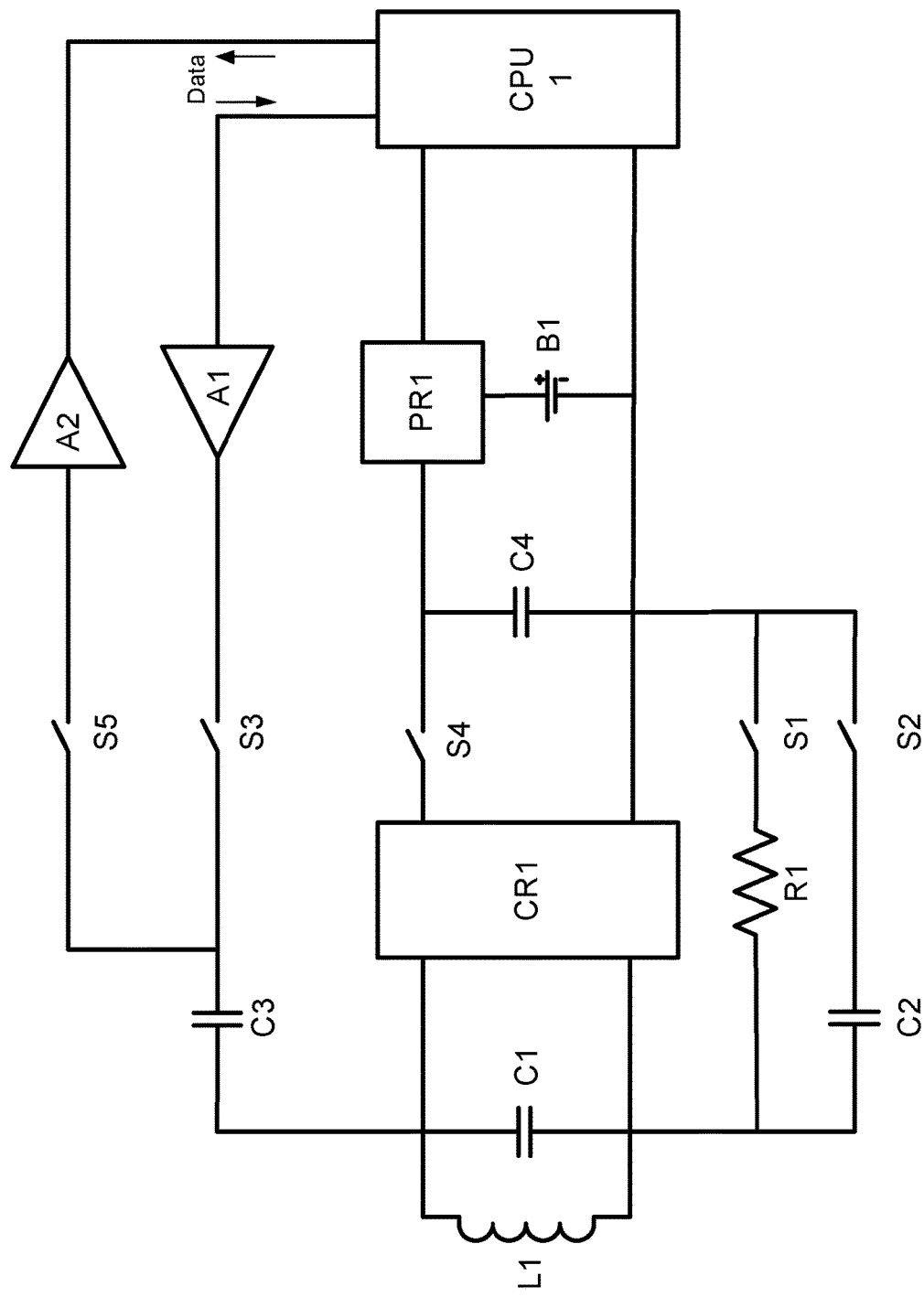
FIG. 2 shows an example of circuit components in one specific embodiment of the present invention.

FIG. 2 shows specific circuit components of one embodiment of such an implantable processor arrangement for an AIMD system implanted under the skin of a patient. An implantable communications coil arrangement is configured for transdermal transfer of an implant communications signal. An implantable processor CPU1 is coupled to and controls the implantable communications coil arrangement that includes parallel tank circuit L1-C1 so as to operate in two different communications modes. Although L1-C1 in FIG. 2 is shown as a parallel tank circuit, it is understood that a series tank circuit L1-C1 may be equivalently used.

In a normal operation mod, the processor CPU1 configures the communications coil arrangement for conventional peridermal communication to receive signals transmitted by an external communications coil placed on the skin of the patient immediately over the implanted L1 coil of the communications coil arrangement. Parallel tank L1-C1 has a resonance frequency that is preferably the same as the frequency of the communications signal transmitted by the external coil. The received signal developed by L1-C1 is rectified by CR1 and passes through closed switch S4 over filtering capacitor C4 to power regulator PR1, which charges the implant battery B1. The data component of the received signal is picked up at L1-C1 and capacitively coupled to an conventional known receiver module (not shown, e.g. an envelope-detector) connected to the implant processor CPU1 which develops the stimulation signals for output to the other implanted components such as to the stimulation contacts on a cochlear implant electrode array. The receiver may be realized by closing switch S5 and utilizing Amplifier A2. The remaining control switches S2 and S3 are open in the normal operations mode to remove their associated components from operation of the implant. In one embodiment, control switch S1 and load resistor R1 are implemented to provide conventional load modulation-based telemetry functionality. In a further embodiment, the conventional load modulation-based telemetry function is implemented with capacitor C2 and switch S2. This has the further advantage that then there is no need to have the load resistor R1 and switch S1, but only capacitor C2 and switch S2 are needed. To lower power consumption, data driver A1 and/or low noise amplifier A2 may be disabled.

In a long range telemetry mode, the implant processor CPU1 configures the communications coil arrangement— the resonant tank L1-C1—for extradermal communication with an external telemetry coil located beyond the skin of the patient immediately over the implanted coil. But the long-range mode has no conventional load-modulation functionality. Control switches S1, S4 and S5 are opened and control switches S3 and S2 are closed so that the implant processor CPU1 sends outbound telemetry data to a data driver A1, which modulates that outbound telemetry data signal at the resonance frequency (the carrier frequency) of the resonant tank L1-C1 which creates a modulated and alternating magnetic field that is extradermally transmitted across the skin to telemetry receiver components beyond the peridermal near skin region; for example, 1-2 meters across a surgical operating theater. Coupling capacitors C2 and C3 allow a DC-free coupling of the resonance tank L1-C1 with the data driving circuit.

To receive data, control switch S3 is opened, removing data driver A1 from the circuit, and control switch S5 is closed adding low noise amplifier A2 that amplifies and provides the received long-range data signal from the resonant tank L1-C1 to the implant processor CPU1. The data driver A1 may be disabled to reduce power consumption.

The extradermal mode has the disadvantage of increased power consumption of the implanted components. To mitigate this problem, the extradermal mode may be enabled only when needed, e.g. by periodic short-termed sniffing or a special wakeup-procedure, which may be implemented with appropriate software processes. And it should be understood the power supply components in the implanted arrangement are not limited specifically to a battery as such, and include without limitation more general energy storage such as a storage capacitor suitable for acting as a temporary power supply when in the extradermal mode. Such a storage capacitor could be configured to provide power only during short periods in the extradermal mode when data bursts are transmitted from the AIMD, and then the storage capacitor can be recharged by the received communications signal during the longer periods in between. In addition, an implant system typically does not start sending telemetry data on its own, but rather does so only in response to one or more specific commands from an external device, such that the system as a whole works in a type of master-slave mode. This is useful since the implanted power source has a limited lifetime and a limited capacity so care is taken to not waste the available energy.

During extradermal mode transmission, the power efficiency of the data transmitting components of the AIMD may be improved by optimizing the capacitances C2 and C3. Both capacitances C2 and C3 can be represented by series capacitance $23=C2 \cdot C3/(C2+C3)$. The series capacitance is then chosen such that the resonance peak is at a lower frequency than the resonance frequency of the tank circuit L1-C1 at $f_0=1/(2 \cdot \pi) \cdot (L1 \cdot C1)^{-1/2}$; thereby maximizing the rms current $I_{L1}$ through the coil L1. That may increase the coil current by a factor of 2 or more for the same driving strength (i.e. peak-peak-voltage) delivered by data driver A1. This yields a better detection performance (e.g. induced voltage in the receiver-coil) and/or increased range. On the other hand, if detection performance and range is kept constant, this improvement reduces power consumption, for example by reducing peak-peak-voltage delivered from and/or supply voltage for data driver A1. At the receiver coil, the induced voltage not only relies on the transmitter e.g. $I_{L1}$ coil current, but also is proportional to the transmission carrier frequency. Hence, the product of the implant coil current and the actual transmission frequency is needed for a quantitative evaluation of the quality.

Figure 3:
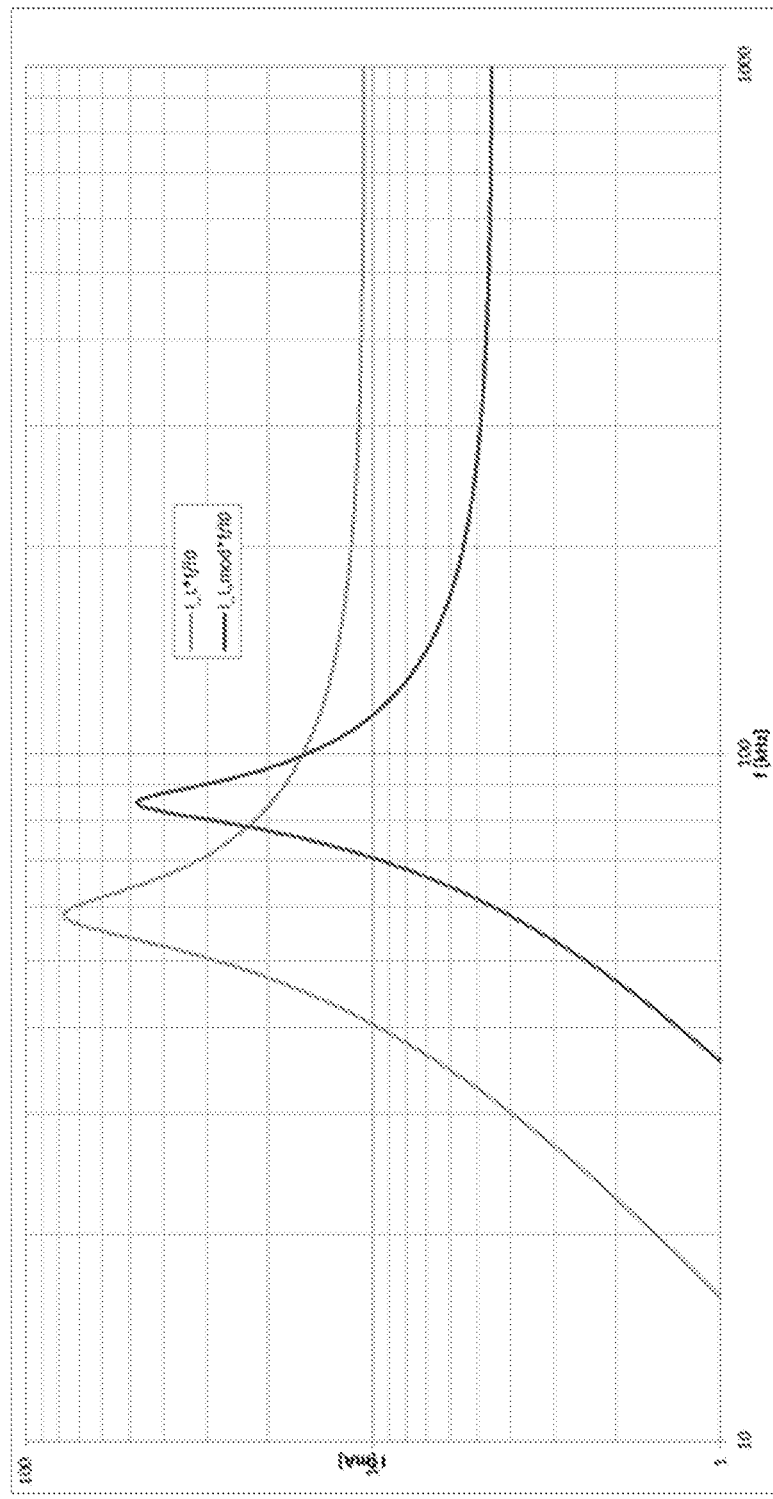
FIG. 3 shows the product of the coil current and transmission carrier frequency normalized by the resonance frequency $f_0$ of the tank circuit in one specific embodiment of the present invention.

FIG. 3 shows the product of the coil current and transmission carrier frequency normalized by the resonance frequency $f_0$ of the tank circuit L1-C1 for L1=10 μH and C1=25.3 nF with 5Ω coil resistance and for example with C23=50 nF and $C23_{mod}$=10 nF as function of the transmission carrier frequency f. In both examples, the resonance peak is below the resonance frequency $f_0$ with 48 mA at 85 kHz and 77 mA at 58 kHz, respectively. This corresponds to an effective increase of 200% and 380% of the voltage induced in the receiver coil.

As just explained, the data transmitting components of the AIMD consume power only during the actual transmission period, but the receiving components need to be enabled and powered over a longer time. Depending on its sensitivity to the received input signal, an AIMD receiver can consume a significant amount of the overall implant power. One way to address that consideration is to define a wakeup-procedure which only activates the AIMD receiver for a short time span within a long time interval; e.g. for 1 millisecond every 1 second, an effective load of 1 permille. If no wakeup-signal is detected during the activation interval, the AIMD receiver is set into a power-saving mode and again reactivated a second later. If a wakeup-signal is detected, then the AIMD receiver may remain active for a defined extradermal mode interval depending on the received data and commands, with the additional constrain that the receiver also may be powered down while the implanted transmitter arrangement is sending back telemetry data.

So depending on the implant function, the AIMD receiver may only be active within a limited specific time span. Extradermal mode data can be transmitted to the external device which then only sends incoming data within the given active time span (this may also include a new wake up). Outside this defined active receive time span the AIMD receiver may be completely shut down without sniffing to conserve a maximum amount of power in the implant. Such extradermal mode data may include a receiver strength signal indicator (RSSI) for each communication partner to indicate to the relevant sender if its transmitted signal is strong enough to be effective, or if it has to be increased, or it may even be decreased to save power.

To enable the extradermal mode, the external programming device may send an extradermal mode request command to the AIMD client and simultaneously start a timer. Upon reception of the command by the AIMD client (either the audio processor or the AIMD implant itself) the AIMD client transmits an acknowledge command to the external programming device using the extradermal link. If the external programming device receives the acknowledgement command while the timer is still running, the extradermal mode link is considered established. The transmission power of the external programming device can be set to a lower level than the one used by the AIMD client to ensure that the programming device receives the acknowledgement. The power level may be predetermined in both the external programming device and the AIMD client, or the external programming device may be able to select an operating power level. In the latter case, the extradermal mode request command may include a power level value used for transmission by the external programming device such that the AIMD client can read the power level value and use it to set its transmission power for extradermal mode transmission such as for the acknowledgement signal. For example, the AIMD client may use the same power level used by the external programming device, or it may increase that power level by a pre-determined amount. This dynamic transmission power negotiation has the advantage to set the AIMD client power level to the smallest needed for reliable extradermal mode communication.

This power level negotiation procedure can be repeated at any time during operation in extradermal mode to dynamically adjust the power needed. For example, the external programming device may issue a power level command periodically, or based on the measured reception signal level or signal quality of the back-telemetry signal. The signal level may be a reception power level value, and/or the signal quality may be a signal to noise ratio (SNR).

To terminate an extradermal mode session, the AIMD client may have a timeout such that when no commands are received for some defined period of time, the AIMD client disables the extradermal mode (e.g., and returns to peridermal mode operation). Or the external programming device may transmit a normal mode request command, which the AIMD client responds to by transmitting an acknowledgement in to the external programming device using the extradermal link and then enters normal range peridermal mode. Of course specific embodiments may include other functions and features such as for information security and/or session control. Such additional features can be added, for example, within or after the wake up procedure.

The extradermal mode eases surgical handling when the implant is tested, and avoids the need to bring the external transmitter coil into close proximity to the wound opening at the patient which has to be kept sterile. Thus conventionally the external transmitter coil has to be sterilized (or placed into a sterile package) before bringing it into close proximity to the patient. But that is no longer necessary with the longer-distance extradermal mode of operation.

Besides testing during implantation surgery, the extradermal mode also may be useful during post-surgical patient fitting sessions. In that case, an external fitting module issues a command to switch the implant processor into the extradermal mode to back telemetry signals for the fitting. This enhances patient comfort during the fitting because no hard cabling is needed.

Some embodiments may also support providing the patient with a remote control to engage the extradermal mode to allow an easy check of the implant state (e.g., battery state) or to change some system settings (on/off, different parameter settings). Moreover, using the extradermal mode of operation the implant system also may communicate with a home monitoring system to transfer log data (as is done for heart pacemakers).

Compared to conventional load modulation telemetry arrangements, little additional circuitry is needed, and an operating frequency band for implant telemetry functions is available worldwide (9 to 315 kHz). The communication coil in the external programming device may need to be relatively large (e.g. more than 10 cm in diameter) and the effective operating distance between external device and internal implant coil may still be rather limited (e.g., 2 meters or less—within the sterile surgical area). But for post-surgical fitting sessions outside the surgical operating theatre, the physician or audiologist may simply place the external communication coil on his desk facing it towards the patient and need not locate the exact position of the implant.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments also can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Embodiments of the present invention may be implemented in various specific AIMD systems, such as, without limitation, cochlear implant systems, totally implantable cochlear implant systems, vestibular implant systems, laryngeal pacemaker systems, middle ear implant systems and bone conduction implant systems. The invention is equally applicable in the external components of these systems or in the implanted components of these systems. Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable processor arrangement for an active implantable medical device (AIMD) system implanted under the skin of a patient, the arrangement comprising:
   an implantable communications coil arrangement configured for transdermal transfer of an implant communications signal; and
   an implantable processor coupled to and controlling the implantable communications coil arrangement so as to operate in two different communications modes:
   i. a normal operation mode wherein the processor configures the communications coil arrangement for peridermal communication with an external communications coil placed on the skin of the patient immediately over the implantable communications coil arrangement using load modulation of the communications coil arrangement, and
   ii. a long range telemetry mode wherein the processor configures the communications coil arrangement for extradermal communication with an external telemetry coil located distant from the skin of the patient immediately over the implantable communications coil arrangement without using load modulation of the communications coil arrangement.

2. The arrangement according to claim 1, wherein the extradermal communication in the long range telemetry mode includes communication of an implant programming signal received by the implantable communications coil arrangement.

3. The arrangement according to claim 1, wherein the extradermal communication in the long range telemetry mode includes communication of an implant telemetry signal transmitted by the implantable communications coil arrangement.

4. The arrangement according to claim 1, wherein the implantable processor controls operation in the long range telemetry mode to be limited in initiation to periodic intervals.

5. The arrangement according to claim 1, wherein the implantable processor controls operation in the long range telemetry mode to be limited in initiation by software control during a defined wake-up procedure.

6. The arrangement according to claim 1, wherein the AIMD system is a cochlear implant system.

7. A fitting system for an active implantable medical device (AIMD) system, the fitting system comprising:
   an external fitting module configured to perform a patient fitting process that adjusts an implanted AIMD processor to reflect patient-specific performance characteristics,
   wherein the AIMD processor has:
   i. a normal operation mode that configures an implanted communications coil arrangement for peridermal communication of an implant communications signal with an external communications coil placed on the skin of the implanted patient immediately over the implanted communications coil arrangement using load modulation of the communications coil arrangement for normal operation of the AIMD system, and
   ii. a long range telemetry mode that configures the implanted communications coil arrangement for extradermal communication with an external telemetry coil located distant from the skin of the implanted patient immediately over the implantable communications coil arrangement without using load modulation of the communications coil arrangement; and
   wherein the patient fitting process includes interaction of the external fitting module via the external telemetry coil with the AIMD processor in the long range telemetry mode to adjust the operation of the AIMD processor in the normal operation mode based on the patient-specific performance characteristics.

8. The system according to claim 7, wherein the extradermal communication in the long range telemetry mode includes communication of an implant programming signal received by the implantable communications coil system.

9. The system according to claim 7, wherein the extradermal communication in the long range telemetry mode includes communication of an implant telemetry signal transmitted by the implanted communications coil system.

10. The system according to claim 7, wherein the AIMD processor controls operation in the long range telemetry mode to be limited in initiation to periodic intervals.

11. The system according to claim 7, wherein the AIMD processor controls operation in the long range telemetry mode to be limited in initiation by software control during a defined wake-up procedure.

12. The system according to claim 7, wherein the AIMD system is a cochlear implant system.

13. A testing system for use during surgical implantation of an active implantable medical device (AIMD) system, the testing system comprising:
   an implantable communications coil arrangement configured for transdermal transfer of an implant communications signal; and
   an implantable processor coupled to and controlling the implantable communications coil arrangement so as to operate in two different communications modes:
   i. a normal operation mode wherein the processor configures the communications coil arrangement for peridermal communication with an external communications coil placed on the skin of the implanted patient immediately over the implantable communications coil arrangement using load modulation of the communications coil arrangement, and
   ii. a long range telemetry mode wherein the processor configures the communications coil arrangement for extradermal communication with an external telemetry coil located distant from the skin of the implanted patient immediately over the implantable communications coil arrangement without using load modulation of the communications coil arrangement.

14. The system according to claim 13, wherein the extradermal communication in the long range telemetry mode includes communication of an implant programming signal received by the implantable communications coil system.

15. The system according to claim 13, wherein the extradermal communication in the long range telemetry mode includes communication of an implant telemetry signal transmitted by the implantable communications coil system.

16. The system according to claim 13, wherein the implantable processor controls operation in the long range telemetry mode to be limited in initiation to periodic intervals.

17. The system according to claim 13, wherein the implantable processor controls operation in the long range telemetry mode to be limited in initiation by software control during a defined wake-up procedure.

18. The system according to claim 13, wherein the AIMD system is a cochlear implant system.

* * * * *